US008629303B2

(12) United States Patent
Komatsu et al.

(10) Patent No.: US 8,629,303 B2
(45) Date of Patent: Jan. 14, 2014

(54) 5-NORBORNENE-2-SPIRO-α-CYCLOALKANONE-α'-SPIRO-2"-5"-NORBORNENE AND METHOD FOR PRODUCING THE SAME

(75) Inventors: Shinichi Komatsu, Yokohama (JP); Michiaki Adachi, Yokohama (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 0 days.

(21) Appl. No.: 13/577,985

(22) PCT Filed: Feb. 9, 2011

(86) PCT No.: PCT/JP2011/052738

§ 371 (c)(1), (2), (4) Date: Aug. 9, 2012

(87) PCT Pub. No.: WO2011/099517

PCT Pub. Date: Aug. 18, 2011

(65) Prior Publication Data

US 2012/0310013 A1 Dec. 6, 2012

(30) Foreign Application Priority Data

Feb. 9, 2010 (JP) ................................ 2010-026953

(51) Int. Cl.
*C07C 49/653* (2006.01)
*C07C 45/61* (2006.01)

(52) U.S. Cl.
USPC .......................................... 568/351; 568/376

(58) Field of Classification Search
USPC ................................................. 568/351, 376
See application file for complete search history.

(56) References Cited

U.S. PATENT DOCUMENTS

| | | | |
|---|---|---|---|
| 3,326,940 | A | 6/1967 | Dunkel et al. |
| 4,271,079 | A | 6/1981 | Maeda et al. |
| 2009/0182114 | A1 | 7/2009 | Kusaka et al. |

FOREIGN PATENT DOCUMENTS

| | | | |
|---|---|---|---|
| JP | 55-36406 | A | 3/1980 |
| JP | 63-057589 | A | 3/1988 |
| JP | 5-271409 | A | 10/1993 |
| JP | 7-304868 | A | 11/1995 |
| JP | 10-310640 | A | 11/1998 |
| JP | 2001-002670 | A | 1/2001 |
| JP | 2002-255955 | A | 9/2002 |
| JP | 2004-018422 | A | 1/2004 |
| JP | 2005-336246 | A | 12/2005 |
| JP | 2008-031406 | A | 2/2008 |
| JP | 2010-184898 | A | 8/2010 |

OTHER PUBLICATIONS

Cordes et al. Medium Effects on the Rates of Stereomutation of a Pair of Diastereomeric Cyclopropanes. Ground Stabilization in Nucleophilic Solvents Induces Deviation from Solvent Polarity Controlled Behaviour. Journal of the American Chemical Society, 1996, vol. 118, 6241-6251.*

Leuger et al. Synthetic Applications of alpha-Fluoroalkylated Enones. 1. Use as Dienophiles in Diels-Alder Cycloadditons. Journal of Organic Chemistry, 2006, vol. 71, 2735-2739.*

Kataoka Shunro, "Engineering Plastics", Kyoritsu Shuppan Co., Ltd., pp. 88-95, (1987), with English Translation.

Masatoshi Kusama et al., Soluble Polyimides with Polyalicyclic Structure. 3.1 Polyimides from (4arH,8acH)-Decahydro-1t,4t:5c8c-dimethanonaphthalene-2t,3t,6c,7c-tetracarboxylic 2,3:6,7-Dianhydride,Macromolecules, vol. 27, pp. 1117-1123 (1994).

Saishin Poriimido—Kiso to Ouyou—(Current Polyimides—Fundamentals and Applications-), NTS Inc., Chapter 1, Alicyclic polyimides, pp. 388-408, (2002), with English Translation).

International Search Report dated Apr. 19, 2011, issued against International Application No. PCT/JP2011/052738.

International Preliminary Report on Patentability dated Sep. 27, 2012 issued in International Application No. PCT/JP2011/052738 (English Translation).

* cited by examiner

*Primary Examiner* — Sikarl Witherspoon
(74) *Attorney, Agent, or Firm* — Fitch, Even, Tabin & Flannery LLP

(57) ABSTRACT

A 5-norbornene-2-spiro-α-cycloalkanone-α'-spiro-2"-5"-norbornene represented by the following general formula (1):

[Chem. 1]

(1)

[in the formula (1), $R^1$s, $R^2$, and $R^3$ each independently represent a hydrogen atom or the like, and n represents an integer of 0 to 12].

10 Claims, 3 Drawing Sheets

5-NORBORNENE-2-SPIRO-α-CYCLOALKANONE-α'-SPIRO-2"-5"-NORBORNENE AND METHOD FOR PRODUCING THE SAME

CROSS-REFERENCE TO RELATED APPLICATIONS

This Application is a U.S. National Stage Application filed under 35 U.S.C. §371 of International Application PCT/JP2011/052738, filed Feb. 9, 2011, designating the United States, which claims priority from Japanese Patent Application 2010-026953, filed Feb. 9, 2010, the complete disclosures of which are hereby incorporated herein by reference in their entirety for all purposes.

TECHNICAL FIELD

The present invention relates to a 5-norbornene-2-spiro-α-cycloalkanone-α'-spiro-2"-5"-norbornene, and a method for producing the same.

BACKGROUND ART

Conventionally, a wholly aromatic polyimide (trade name "Kapton") has been known as a material necessary for cutting-edge industries for aerospace and aviation applications and the like. The wholly aromatic polyimide is synthesized from a combination of an aromatic tetracarboxylic dianhydride and an aromatic diamine by utilizing a reaction represented by the following reaction formula (I):

[Chem. 1]

[Reaction Formula (I)]

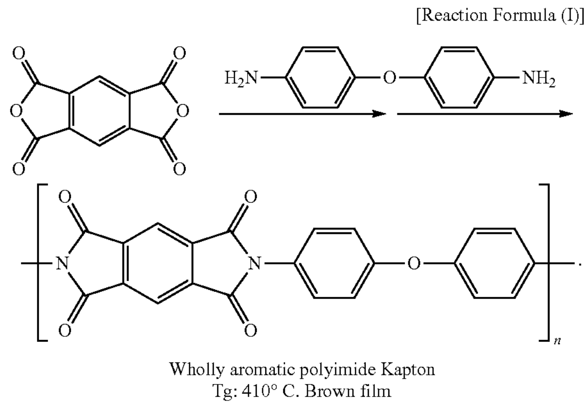

Wholly aromatic polyimide Kapton
Tg: 410° C. Brown film

The wholly aromatic polyimide is known to exhibit one of the highest levels of heat resistance (glass transition temperature (Tg): 410° C.) among heat resistance polymers (see Engineering plastics, Kyoritsu Shuppan Co., Ltd., 1987, p. 88 (NPL 1)). However, the wholly aromatic polyimide is colored in brown, because intramolecular charge transfer (CT) occurs between a tetracarboxylic dianhydride unit of an aromatic ring system and a diamine unit of another aromatic ring system. Hence, the wholly aromatic polyimide cannot be used in optical applications and the like, where transparency is necessary. For this reason, in order to produce a polyimide usable in optical applications and the like, research has been conducted on alicyclic polyimides in which no intramolecular CT occurs, and which has a high light transmittance.

There are three kinds of alicyclic polyimides: one is a combination of an alicyclic tetracarboxylic dianhydride and an alicyclic diamine; another is a combination of an alicyclic tetracarboxylic dianhydride and an aromatic diamine; and the other is a combination of an aromatic tetracarboxylic dianhydride and an alicyclic diamine. However, of these alicyclic polyimides, the ones using an alicyclic diamine are difficult to obtain with high molecular weights. This is because an alicyclic diamine has a basicity which is $10^5$ to $10^6$ times greater than that of an aromatic diamine, and hence the polymerization behavior of an alicyclic diamine is totally different from that of an aromatic diamine, so that a salt precipitates during the polymerization. On the other hand, alicyclic polyimides each obtained by combining an alicyclic tetracarboxylic dianhydride and an aromatic diamine can be produced with direct application of general synthetic procedures for the wholly aromatic polyimide, and are easy to obtain with high molecular weights. For this reason, of the alicyclic polyimides, alicyclic polyimides each obtained by combining an alicyclic tetracarboxylic dianhydride and an aromatic diamine have attracted attention in recent years.

Known alicyclic tetracarboxylic dianhydrides used for producing such alicyclic polyimides include those of a monocyclic ring system, a bicyclic ring system, a tricyclic ring system, a tetracyclic ring system, a spiro ring system, and the like. For example, as an alicyclic polyimide using an alicyclic tetracarboxylic dianhydride of a tetracyclic ring system, an alicyclic polyimide is known which is obtained from a dimethanonaphthalene-type tetracarboxylic dianhydride by utilizing a reaction represented by the following reaction formula (II) (see Macromolecules, vol. 27, 1994, p. 1117 (NPL 2)):

[Chem. 2]

[Reaction Formula (II)]

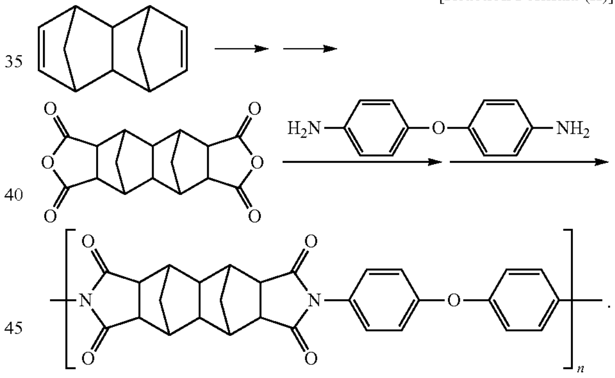

Alicyclic polyimide Tg: 404° C. Colorless and transparent film
Macromolecules, 1994, 27, 1117

In addition, the alicyclic polyimide obtained from the dimethanonaphthalene-type tetracarboxylic dianhydride is also known to exhibit a heat resistance (glass transition temperature (Tg): 404° C.) close to that of the wholly aromatic polyimide (see SAISHIN PORIIMIDO-KISO TO OUYOU-(Current Polyimides-Fundamentals and Applications-), NTS INC., 2002, Chapter 1, alicyclic polyimides, p. 388 (NPL 3)). In addition, as for other alicyclic tetracarboxylic dianhydrides, the followings are disclosed, for example. Specifically, Japanese Unexamined Patent Application Publication No. Sho 55-36406 (PTL 1) discloses 5-(2,5-dioxotetrahydro-3-furanyl)-3-methyl-3-cyclohexene-1,2-dicarboxylic anhydride. Meanwhile, Japanese Unexamined Patent Application Publication No. Sho 63-57589 (PTL 2) discloses bicyclo[2.2.1]heptane-2,3,5,6-tetracarboxylic dianhydrides. In addition, Japanese Unexamined Patent Application Publication No. Hei 7-304868 (PTL 3) discloses bicyclo[2.2.2]octanetetracarboxylic dianhydrides as raw materials of polyimide resins. Moreover, Japanese Unexamined Patent Application Publication No. 2001-2670 (PTL 4) and Japanese Unexamined Patent Application Publication No. 2002-255955 (PTL 5) disclose 1,2-bis(4'-oxa-3',5'-dioxotricyclo[$5.2.1.0^{2,6}$]decane-8'-yloxy)ethane. Furthermore, Japanese Unexamined Patent Application Publication No. Hei 10-310640 (PTL 6) discloses bicyclo[2.2.1]heptane-2,3,5-tricarboxyl-5-acetic 2,3:5,5-dianhydride. However, no polyimide having a sufficiently high level of heat resistance can be produced, when an alicyclic polyimide is produced by utilizing any of such conventional alicyclic tetracarboxylic dianhydrides.

CITATION LIST

Patent Literature

[PTL 1] Japanese Unexamined Patent Application Publication No. Sho 55-36406

[PTL 2] Japanese Unexamined Patent Application Publication No. Sho 63-57589

[PTL 3] Japanese Unexamined Patent Application Publication No. Hei 7-304868

[PTL 4] Japanese Unexamined Patent Application Publication No. 2001-2670

[PTL 5] Japanese Unexamined Patent Application Publication No. 2002-255955

[PTL 6] Japanese Unexamined Patent Application Publication No. Hei 10-310640

Non Patent Literature

[NPL1] Engineering plastics, Kyoritsu Shuppan Co., Ltd., published in 1987, p. 88

[NPL 2] Macromolecules, vol. 27, published in 1994, p. 1117

[NPL 3] SAISHIN PORIIMIDO-KISO TO OUYOU-(Current Polyimides-Fundamentals and Applications-), NTS INC., 2002, Chapter 1, alicyclic polyimides, p. 388

SUMMARY OF INVENTION

Technical Problem

The present invention has been made in view of the problems of the conventional technologies, and an object of the present invention is to provide a 5-norbornene-2-spiro-α-cycloalkanone-α'-spiro-2"-5"-norbornene which can be preferably used as a raw material compound of an alicyclic tetracarboxylic dianhydride used for producing an alicyclic polyimide having a high light transmittance and a sufficiently high level of heat resistance, and a method for producing a 5-norbornene-2-spiro-α-cycloalkanone-α'-spiro-2"-5"-norbornene, the method making it possible to efficiently produce a 5-norbornene-2-spiro-α-cycloalkanone-α'-spiro-2"-5"-norbornene in a sufficiently high yield.

Solution to Problem

The present inventors have conducted earnest study to achieve the above-described object. As a result, the present inventors have found that a compound having a structure represented by the following general formula (1) makes it possible to produce an alicyclic tetracarboxylic dianhydride for obtaining an alicyclic polyimide having a sufficiently high level of heat resistance. This finding has led to the completion of the present invention.

Specifically, the 5-norbornene-2-spiro-α-cycloalkanone-α'-spiro-2"-5"-norbornene of the present invention is represented by the following general formula (1):

[Chem. 3]

(1)

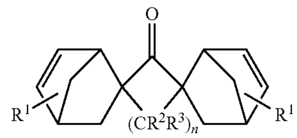

[in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12].

Note that, although it is not exactly clear why an alicyclic polyimide having a sufficiently high level of heat resistance can be obtained, when a tetracarboxylic dianhydride is produced from the 5-norbornene-2-spiro-α-cycloalkanone-α'-spiro-2"-5"-norbornene represented by the general formula (1), and the alicyclic polyimide is produced by using the tetracarboxylic dianhydride, the present inventors speculate as follows. Specifically, the 5-norbornene-2-spiro-α-cycloalkanone-α'-spiro-2"-5"-norbornene represented by the general formula (1) has a chemically sufficiently stable structure, because the structure has a ketone group being capable of improving the heat resistance of a polyimide and being a polar group not inhibiting the polymerization reaction, and has no active α hydrogen remaining on carbon atoms adjacent to the ketone of the ketone group-containing norbornene. Hence, when a polyimide is produced by using the 5-norbornene-2-spiro-α-cycloalkanone-α'-spiro-2"-5"-norbornene, a higher level of heat resistance can be achieved.

In addition, a method for producing a 5-norbornene-2-spiro-α-cycloalkanone-α'-spiro-2"-5"-norbornene of the present invention is a method comprising:

a first step of forming a Mannich base by reacting a carbonyl compound and an amine compound with each other in an acidic solvent, to thereby obtain a reaction liquid comprising the Mannich base in the acidic solvent,

- the acidic solvent comprising a formaldehyde derivative and 0.01 mol/L or more of an acid represented by a formula: HX (in the formula, X represents one selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$),
- the carbonyl compound being represented by the following general formula (2):

[Chem. 4]

(2)

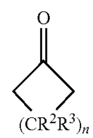

[in the formula (2), $R^2$ and $R^3$ each independently represent one selected from the group consisting of a hydrogen atom, alkyl groups having 1 to 10 carbon atoms, and a fluorine atom, and n represents an integer of 0 to 12], the amine compound being represented by the following general formula (3):

[Chem. 5]

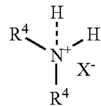

(3)

[in the formula (3), $R^4$s each independently represent one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, and saturated hydrocarbon groups having a hydroxyl group and 1 to 10 carbon atoms, the two $R^4$s may be bonded to each other to form a ring selected from the group consisting of a pyrrolidine ring, a piperidine ring, a piperazine ring, and a morpholine ring, and $X^-$ represents one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$], the Mannich base being represented by the following general formula (4):

[Chem. 6]

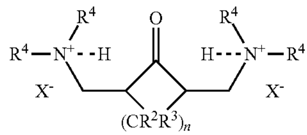

(4)

[$R^2$, $R^3$, and n in the formula (4) have the same meanings as those of $R^2$, $R^3$, and n in the formula (2), and $R^4$s and $X^-$s in the formula (4) have the same meanings as those of $R^4$s and $X^-$ in the formula (3)]; and a second step of reacting the Mannich base and a diene compound with each other by adding an organic solvent, a base in an amount of 1.0 to 20.0 equivalents to the acid, and the diene compound to the reaction liquid, and then heating the reaction liquid, to thereby form a 5-norbornene-2-spiro-α-cycloalkanone-α'-spiro-2"-5"-norbornene, the diene compound being represented by the following general formula (5):

[Chem. 7]

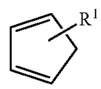

(5)

[in the formula (5), $R^1$ represents one selected from the group consisting of a hydrogen atom, alkyl groups having 1 to 10 carbon atoms, and a fluorine atom], the 5-norbornene-2-spiro-α-cycloalkanone-α'-spiro-2"-5"-norbornene being represented by the following general formula (1):

[Chem. 8]

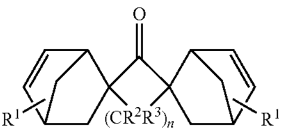

(1)

[$R^1$s in the formula (1) have the same meaning as that of $R^1$ in the formula (5), and $R^2$, $R^3$, and n in the formula (1) have the same meanings as those of $R^2$, $R^3$, and n in the formula (2)].

In the method for producing a 5-norbornene-2-spiro-α-cycloalkanone-α'-spiro-2"-5"-norbornene of the present invention, the acidic solvent preferably comprises 0.01 to 2.0 mol/L of the acid. In addition, the base is preferably at least one selected from the group consisting of amines, alkali metal hydroxides, and alkaline earth metal hydroxides. In addition, the amount of the base added to the reaction liquid is preferably 1.0 to 20.0 equivalents, and more preferably 1.0 to 10.0 equivalents to the acid. Moreover, a heating temperature in the second step is preferably 30 to 180° C.

In addition, in the method for producing a 5-norbornene-2-spiro-α-cycloalkanone-α'-spiro-2"-5"-norbornene of the present invention, the organic solvent added to the reaction liquid is preferably an organic solvent immiscible with a saturated hydrocarbon having 5 to 30 carbon atoms. This enables liquid-liquid extraction of the 5-norbornene-2-spiro-α-cycloalkanone-α'-spiro-2"-5"-norbornene directly from the reaction liquid with the saturated hydrocarbon having 5 to 30 carbon atoms, so that the step can be simplified. Accordingly, in the present invention, it is preferable that the organic solvent added to the reaction liquid be an organic solvent immiscible with a saturated hydrocarbon having 5 to 30 carbon atoms, and that, after the reaction, the 5-norbornene-2-spiro-α-cycloalkanone-α'-spiro-2"-5"-norbornene be liquid-liquid extracted directly from the reaction liquid with the saturated hydrocarbon having 5 to 30 carbon atoms.

In addition, in the method for producing a 5-norbornene-2-spiro-α-cycloalkanone-α'-spiro-2"-5"-norbornene of the present invention, it is also possible to use, as the organic solvent, an organic solvent miscible with a saturated hydrocarbon having 5 to 30 carbon atoms. In this case, it is preferable to comprise a step in which after the 5-norbornene-2-spiro-α-cycloalkanone-α'-spiro-2"-5"-norbornene is formed in the second step, the organic solvent miscible with the saturated hydrocarbon having 5 to 30 carbon atoms is removed; and while an obtained mixture is used as it is or with water being added to the obtained mixture, the 5-norbornene-2-spiro-α-cycloalkanone-α'-spiro-2"-5"-norbornene is separated by extraction with the saturated hydrocarbon having 5 to 30 carbon atoms. Specifically, in the step of separation by extraction, it is preferable that a mixture be obtained by removing the organic solvent, and then, while an obtained mixture is used as it is or with water added to the obtained mixture as appropriate, the 5-norbornene-2-spiro-α-cycloalkanone-α'-spiro-2"-5"-norbornene be separated by extraction with the saturated hydrocarbon having 5 to 30 carbon atoms. In addition, it is more preferable to further comprise, after the step of separation by extraction (including the step of performing liquid-liquid extraction), a step of washing, with an aqueous alkali solution and an aqueous acid solution, an extraction liquid which is obtained by separating the 5-norbornene-2-spiro-α-cycloalkanone-α'-spiro-2"-5"-norbornene by extraction with the saturated hydrocarbon having 5 to 30 carbon atoms, and which comprises the 5-norbornene-2-spiro-α-cycloalkanone-α'-spiro-2"-5"-norbornene and the saturated hydrocarbon.

Advantageous Effects of Invention

According to the present invention, it is possible to provide a 5-norbornene-2-spiro-α-cycloalkanone-α'-spiro-2"-5"-norbornene which can be preferably used as a raw material compound of an alicyclic tetracarboxylic dianhydride used for producing an alicyclic polyimide having a high light transmittance and a sufficiently high level of heat resistance, and a method for producing a 5-norbornene-2-spiro-α-cycloalkanone-α'-spiro-2"-5"-norbornene, the method making it possible to efficiently produce a 5-norbornene-2-spiro-α-cycloalkanone-α'-spiro-2"-5"-norbornene in a sufficiently high yield.

DESCRIPTION OF EMBODIMENTS

Figure 1:
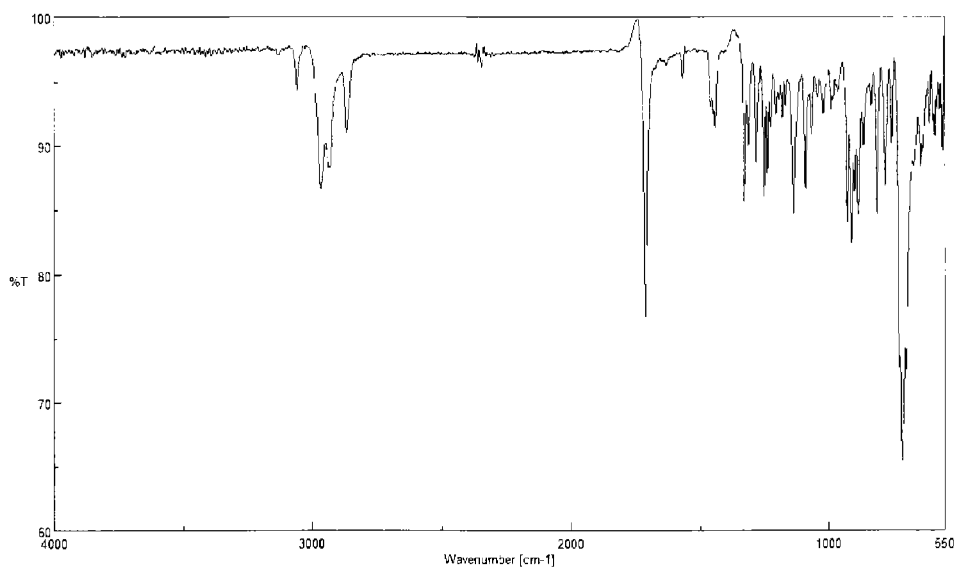
FIG. 1 is a graph showing an IR spectrum of 5-norbornene-2-spiro-2'-cyclopentanone-5'-spiro-2"-5"-norbornene obtained in Example 1.

Hereinafter, the present invention will be described in detail based on preferred embodiments thereof.

First, a 5-norbornene-2-spiro-α-cycloalkanone-α'-spiro-2"-5"-norbornene of the present invention is described. Specifically, the 5-norbornene-2-spiro-α-cycloalkanone-α'-spiro-2"-5"-norbornene of the present invention is represented by the following general formula (1):

[Chem. 9]

(1)

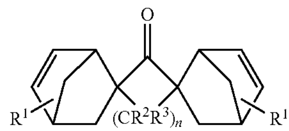

[in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12].

Note that, in the following description, the 5-norbornene-2-spiro-α-cycloalkanone-α'-spiro-2"-5"-norbornene represented by the general formula (1) is simply referred to as a "bis(spiro norbornene)" in some cases.

The alkyl group which can be selected as each $R^1$ in the general formula (1) is an alkyl group having 1 to 10 carbon atoms. If the number of carbon atoms of the alkyl group exceeds 10, the heat resistance of an obtained polyimide is lowered in the use as a monomer for the polyimide. In addition, the number of carbon atoms of the alkyl group which can be selected as each $R^1$ is preferably 1 to 5, and more preferably 1 to 3, from the viewpoint that a higher level of heat resistance is obtained when a polyimide is produced. In addition, the alkyl group which can be selected as each $R^1$ may be linear chain or branched.

$R^1$s in the general formula (1) are each independently more preferably a hydrogen atom or an alkyl group having 1 to 10 carbon atoms, from the viewpoint that a higher level of heat resistance is obtained when a polyimide is produced. Especially, $R^1$s in the general formula (1) are each independently more preferably a hydrogen atom, a methyl group, an ethyl group, a n-propyl group, or an isopropyl group, and particularly preferably a hydrogen atom or a methyl group, from the viewpoints that raw materials are readily available, and that purification is easier. In addition, the plural $R^1$s in the formula are particularly preferably the same, from the viewpoints of ease of purification and the like.

In addition, n in the general formula (1) represents an integer of 0 to 12. If the value of n exceeds the upper limit, it becomes difficult to purify the bis(spiro norbornene) represented by the general formula (1). In addition, an upper limit value of the numeric value range of n in the general formula (1) is more preferably 5, and particularly preferably 3, from the viewpoint that the purification of the bis(spiro norbornene) becomes easier. Meanwhile, a lower limit value of the numeric value range of n in the general formula (1) is more preferably 1, and particularly preferably 2, from the viewpoint of the stability of a raw material. Accordingly, n in the general formula (1) is particularly preferably an integer of 2 to 3.

In addition, the alkyl groups having 1 to 10 carbon atoms which can be selected as $R^2$ or $R^3$ in the general formula (1) are the same as the alkyl groups having 1 to 10 carbon atoms which can be selected as each $R^1$. Of these substituents, the substituent which can be selected as $R^2$ or $R^3$ is preferably a hydrogen atom, and an alkyl group having 1 to 10 (more preferably 1 to 5, further preferably 1 to 3) carbon atoms, and particularly preferably a hydrogen atom or a methyl group, from the viewpoint of ease of purification.

Specific examples of the bis(spiro norbornene) represented by the general formula (1) include 5-norbornene-2-spiro-α-cyclopentanone-α'-spiro-2"-5"-norbornene (also referred to as "5-norbornene-2-spiro-2'-cyclopentanone-5'-spiro-2"-5"-norbornene"), methyl-5-norbornene-2-spiro-α-cyclopentanone-α'-spiro-2"-(methyl-5"-norbornene), 5-norbornene-2-spiro-α-cyclohexanone-α'-spiro-2"-5"-norbornene (also referred to as "5-norbornene-2-spiro-2'-cyclohexanone-6'-spiro-2"-5"-norbornene"), methyl-5-norbornene-2-spiro-α-cyclohexanone-α'-spiro-2"-(methyl-5"-norbornene), 5-norbornene-2-spiro-α-cyclopropanone-α'-spiro-2"-5"-norbornene, 5-norbornene-2-spiro-α-cyclobutanone-α'-spiro-2"-5"-norbornene, 5-norbornene-2-spiro-α-cycloheptanone-α'-spiro-2"-5"-norbornene, 5-norbornene-2-spiro-α-cyclooctanone-α'-spiro-2"-5"-norbornene, 5-norbornene-2-spiro-α-cyclononanone-α'-spiro-2"-5"-norbornene, 5-norbornene-2-spiro-α-cyclodecanone-α'-spiro-2"-5"-norbornene, 5-norbornene-2-spiro-α-cycloundecanone-α'-spiro-2"-5"-norbornene, 5-norbornene-2-spiro-α-cyclododecanone-α'-spiro-2"-5"-norbornene, 5-norbornene-2-spiro-α-cyclotridecanone-α'-spiro-2"-5"-norbornene, 5-norbornene-2-spiro-α-cyclotetradecanone-α'-spiro-2"-5"-norbornene, 5-norbornene-2-spiro-α-cyclopentadecanone-α'-spiro-2"-5"-norbornene, 5-norbornene-2-spiro-α-(methylcyclopentanone)-α'-spiro-2"-5"-norbornene, 5-norbornene-2-spiro-α-(methylcyclohexanone)-α'-spiro-2"-5"-norbornene,and the like.

Next, a description is given of a method for producing a 5-norbornene-2-spiro-α-cycloalkanone-α'-spiro-2"-5"-norbornene of the present invention, which is preferable as a method for producing the 5-norbornene-2-spiro-α-cycloalkanone-α'-spiro-2"-5"-norbornene (the bis(spiro norbornene)) of the present invention.

The method for producing a 5-norbornene-2-spiro-α-cycloalkanone-α'-spiro-2"-5"-norbornene of the present invention is a method comprising:

a first step of forming a Mannich base by reacting a carbonyl compound and an amine compound with each other in an acidic solvent, to thereby obtain a reaction liquid comprising the Mannich base in the acidic solvent, the acidic solvent comprising a formaldehyde derivative and 0.01 mol/L or more of an acid represented by a formula: HX (in the formula, X represents one selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$), the carbonyl compound being represented by the following general formula (2):

[Chem. 10]

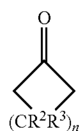

(2)

[in the formula (2), $R^2$ and $R^3$ each independently represent one selected from the group consisting of a hydrogen atom, alkyl groups having 1 to 10 carbon atoms, and a fluorine atom, and n represents an integer of 0 to 12], the amine compound being represented by the following general formula (3):

[Chem. 11]

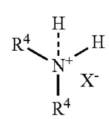

(3)

[in the formula (3), $R^4$s each independently represent one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, and saturated hydrocarbon groups having a hydroxyl group and 1 to 10 carbon atoms, the two $R^4$s may be bonded to each other to form a ring selected from the group consisting of a pyrrolidine ring, a piperidine ring, a piperazine ring, and a morpholine ring, and $X^-$ represents one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$], the Mannich base being represented by the following general formula (4):

[Chem. 12]

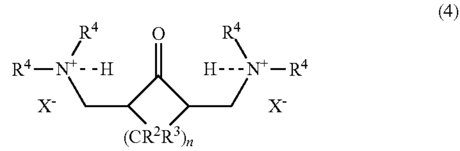

(4)

[$R^2$, $R^3$, and n in the formula (4) have the same meanings as those of $R^2$, $R^3$, and n in the formula (2), and $R^4$s and $X^-$s in the formula (4) have the same meanings as those of $R^4$s and $X^-$ in the formula (3)]; and a second step of reacting the Mannich base and a diene compound with each other by adding an organic solvent, a base in an amount of 1.0 to 20.0 equivalents to the acid, and the diene compound to the reaction liquid, and then heating the reaction liquid, to thereby form a 5-norbornene-2-spiro-α-cycloalkanone-α'-spiro-2"-5"-norbornene, the diene compound being represented by the following general formula (5):

[Chem. 13]

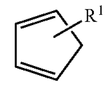

(5)

[in the formula (5), $R^1$ represents one selected from the group consisting of a hydrogen atom, alkyl groups having 1 to 10 carbon atoms, and a fluorine atom], the 5-norbornene-2-spiro-α-cycloalkanone-α'-spiro-2"-5"-norbornene being represented by the general formula (1). The first step and the second step are described separately below.

(First Step)

The first step is a step of forming the Mannich base represented by the general formula (4) by reacting the carbonyl compound represented by the general formula (2) and the amine compound represented by the general formula (3) with each other in the acidic solvent, to thereby obtain the reaction liquid comprising the Mannich base in the acidic solvent.

The acidic solvent used in the first step comprises a formaldehyde derivative. The formaldehyde derivative is not particularly limited, as long as the formaldehyde derivative can be used for producing a so-called Mannich base. Examples of the formaldehyde derivative include formalin, paraformaldehyde, trioxane, 1,3-dioxolane, 1,3-dioxole, 1,3-dioxane, 1,3-dioxin, 1,3-dioxepane, dihydro-1,3-dioxepin, 1,3-dioxepin, 1,3-dioxocane, dihydro-1,3-dioxocin, 1,3-dioxocin, formaldehyde dimethyl acetal, formaldehyde diethyl acetal, formaldehyde dipropyl acetal, formaldehyde dibutyl acetal, formaldehyde diphenyl acetal, and the like.

In addition, of these formaldehyde derivatives, formalin, paraformaldehyde, trioxane, and 1,3-dioxolane are preferable, and formalin, paraformaldehyde are more preferable, from the viewpoint of availability. In addition, one of these formaldehyde derivatives alone or a combination of two or more thereof may be used. However, one of these formaldehyde derivatives alone is preferably used from the viewpoint of purification.

The content of the formaldehyde derivative in the acidic solvent is preferably 2.0 to 50.0% by mass, and more preferably 4.0 to 25.0% by mass. If the content of the formaldehyde derivative is less than the lower limit, the yield of the Mannich base represented by the general formula (4) tends to be low. Meanwhile, if the content exceeds the upper limit, the yield tends to be low, and purification tends to be difficult.

In addition to the formaldehyde derivative, the acidic solvent used in the first step comprises the acid represented by the formula: HX (in the formula, X represents any selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$).

The kind of the acid (HX) is not particularly limited, as long as the acid is represented by the formula: HX. From the viewpoint of the stability of the Mannich base represented by the general formula (4) in the acidic solvent, an acid whose X in the formula is F, Cl, Br, $CH_3COO$, or $CF_3COO$ is more preferable, and an acid whose X in the formula is Cl or $CH_3COO$ is further preferable. In the acidic solvent, the content of the acid (HX) needs to be 0.01 mol/L or more (more preferably 0.01 to 2.0 mol/L, further preferably 0.02 to 2.0 mol/L, and particularly preferably 0.04 to 1.0 mol/L). If the content of the acid is less than the lower limit, the yield of the Mannich base prepared in the first step is insufficient, so that it is impossible to prepare the bis(spiro norbornene) represented by the general formula (1) sufficiently and efficiently. Meanwhile, if the content of the acid (HX) exceeds the upper limit, the yield tends to be low, and the purification tends to be difficult.

Moreover, the acidic solvent may comprise a solvent, other than the formaldehyde derivative and the acid. Examples of the solvent include water, alcohols, glycols, glycerin, ethers, cellosolves, nitriles, amides, and the like. In addition, the content of the solvent in the acidic solvent is preferably 20 to 60% by mass, and more preferably 30 to 50% by mass. If the content of the solvent is less than the lower limit, the mixing tends to be non-uniform, so that the yield of the Mannich base tends to be low. Meanwhile, if the content of the solvent exceeds the upper limit, the reaction rate tends to be lowered, so that the yield tends to decrease.

In addition, in the first step, the use of the acidic solvent comprising the formaldehyde derivative and 0.01 mol/L or more of the acid (the acid represented by the formula: HX) enables the carbonyl compound and the amino compound to react with each other under an acidic condition where the acid is present in excess. This makes it possible to efficiently produce the Mannich base represented by the general formula (4), which is a reaction intermediate used for the preparation of the bis(spiro norbornene).

In addition, the carbonyl compound used in the first step is represented by the following general formula (2):

[Chem. 14]

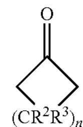

(2)

[in the formula (2), $R^2$ and $R^3$ each independently represent one selected from the group consisting of a hydrogen atom, alkyl groups having 1 to 10 carbon atoms, and a fluorine atom, and n represents an integer of 0 to 12].

In addition, the substituents which can be selected as $R^2$ or $R^3$ in the general formula (2) are the same as the substituents which can be selected as $R^2$ or $R^3$ in the general formula (1). Of these substituents, the substituent which can be selected as $R^2$ or $R^3$ is preferably a hydrogen atom, or an alkyl group having 1 to 10 (more preferably 1 to 5, and further preferably 1 to 3) carbon atoms, and particularly preferably a hydrogen atom or a methyl group, from the viewpoint of ease of purification. Moreover, n in the general formula (2) is the same integer as that for n in the general formula (1), and preferred values thereof are the same as those of n in the general formula (1).

Examples of the carbonyl compound represented by the general formula (2) include cyclopropanone, cyclobutanone, cyclopentanone, cyclohexanone, cycloheptanone, cyclooctanone, cyclononanone, cyclodecanone, cycloundecanone, cyclododecanone, cyclotridecanone, cyclotetradecanone, cyclopentadecanone, 3-methylcyclobutanone, 3-methylcyclopentanone, 3-methylcyclohexanone, 3-methylcycloheptanone, 3-methylcyclooctanone, 3-methylcyclononanone, 3-methylcyclodecanone, 3-methylcycloundecanone, 3-methylcyclododecanone, 3-methylcyclotridecanone, 3-methylcyclotetradecanone, 3-methylcyclopentadecanone, 3-fluorocyclobutanone, 3-fluorocyclopentanone, 3-fluorocyclohexanone, 3-fluorocycloheptanone, 3-fluorocyclooctanone, 3-fluorocyclononanone, 3-fluorocyclodecanone, 3-fluorocycloundecanone, 3-fluorocyclododecanone, 3-fluorocyclotridecanone, 3-fluorocyclotetradecanone, 3-fluorocyclopentadecanone, 3,4-dimethylcyclopentanone, 3,4-dimethylcyclohexanone, 3,5-dimethylcyclohexanone, 3,4,5-trimethylcyclohexanone, 3,4-difluorocyclopentanone, 3,4-difluorocyclohexanone, 3,5-difluorocyclohexanone, 3,4,5-trifluorocyclohexanone, 3,3,4,4-tetrafluorocyclopentanone, 3,3,4,4,5,5-hexafluorocyclohexanone, and the like.

In addition, the method for preparing the carbonyl compound represented by the general formula (2) is not particularly limited, and a known method can be employed as appropriate. Moreover, as the compound represented by the general formula (2), a commercially available product may be used.

In addition, the amine compound used in the first step is represented by the following general formula (3):

[Chem. 15]

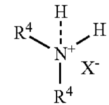

(3)

[in the formula (3), $R^4$s each independently represent any one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, and saturated hydrocarbon groups having a hydroxyl group and 1 to 10 carbon atoms, the two $R^4$s may be bonded to each other to form a ring selected from the group consisting a pyrrolidine ring, a piperidine ring, a piperazine ring, and a morpholine ring, and $X^-$ represents one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$].

The linear chain saturated hydrocarbon group which can be selected as each $R^4$ in the general formula (3) is one having 1 to 20 carbon atoms. The linear chain saturated hydrocarbon group has more preferably 1 to 10 carbon atoms, and further preferably 1 to 5 carbon atoms. If the number of carbon atoms of the linear chain saturated hydrocarbon group exceeds the upper limit, the purification tends to be difficult. As the linear chain saturated hydrocarbon group which can be selected as each $R^4$, a methyl group or an ethyl group is more preferable, from the viewpoint of ease of purification.

Meanwhile, the branched chain saturated hydrocarbon group which can be selected as each $R^4$ is one having 3 to 20 carbon atoms. The branched chain saturated hydrocarbon group has more preferably 3 to 10 carbon atoms, and further preferably 3 to 5 carbon atoms. If the number of carbon atoms of the branched chain saturated hydrocarbon group exceeds the upper limit, the purification tends to be difficult. As the branched chain saturated hydrocarbon groups which can be selected as each $R^4$, an isopropyl group is more preferable, from the viewpoint of ease of purification.

Moreover, the saturated cyclic hydrocarbon group which can be selected as each $R^4$ is one having 3 to 20 carbon atoms. The saturated cyclic hydrocarbon group has more preferably 3 to 10 carbon atoms, and further preferably 5 to 6 carbon atoms. If the number of carbon atoms of the saturated cyclic hydrocarbon group exceeds the upper limit, the purification becomes difficult. Meanwhile, if the number of carbon atoms is less than the lower limit, chemical stability tends to decrease. As the saturated cyclic hydrocarbon group which can be selected as each $R^4$, a cyclopentyl group or a cyclohexyl group is more preferable, from the viewpoints of ease of purification and of chemical stability.

The saturated hydrocarbon group having a hydroxyl group which can be selected as each $R^4$ is one whose hydrocarbon group has 1 to 10 carbon atoms. In the saturated hydrocarbon group having a hydroxyl group, the number of carbon atoms is more preferably 2 to 10, and further preferably 2 to 5. If the number of carbon atoms of the saturated hydrocarbon group having a hydroxyl group exceeds the upper limit, the purification becomes difficult. Meanwhile, if the number of carbon atoms is less than the lower limit, chemical stability tends to be poor. As the saturated hydrocarbon group having a hydroxyl group which can be selected as each $R^4$, a 2-hydroxyethyl group is more preferable from the viewpoints of ease of purification and of chemical stability.

In addition, the two $R^4$s in the general formula (3) may be bonded to each other to form any ring of a pyrrolidine ring, a piperidine ring, a piperazine ring, and a morpholine ring. Specifically, regarding the two $R^4$s in the general formula (3), the $R^4$s may be bonded to each other to form a pyrrolidine ring, a piperidine ring, a piperazine ring, or a morpholine ring, together with the nitrogen atom (N) in the formula (3). When the $R^4$s are bonded to each other to form a ring as described above, morpholine is more preferable from the viewpoint of odor. Moreover, as $R^4$s in the general formula (3), a methyl group, an ethyl group, a 2-hydroxyethyl group, or morpholine is more preferable, from the viewpoint of ease of purification.

$X^-$ in the general formula (3) is a so-called counter anion. $X^-$ is any one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$. $X^-$ is preferably $F^-$, $Cl^-$, $Br^-$, $CH_3COO^-$, or $CF_3COO^-$, and more preferably $Cl^-$ or $CH_3COO^-$, from the viewpoint of the stability of the obtained Mannich base represented by the general formula (4).

In addition, examples of the amine compound represented by the general formula (3) include salts (secondary amine salts in which the aforementioned $X^-$ serves as a counter anion) of secondary amines such as dimethylamine, diethylamine, di-n-propylamine, diisopropylamine, di-n-butylamine, diisobutylamine, di-sec-butylamine, di-t-butylamine, dipentylamine, dicyclopentylamine, dihexylamine, dicyclohexylamine, diheptylamine, dioctylamine, di(2-ethylhexyl) amine, dinonylamine, didecylamine, diundecylamine, didodecylamine, ditridecylamine, ditetradecylamine, dipentadecylamine, dihexadecylamine, diheptadecylamine, dioctadecylamine, dinonadecylamine, morpholine, diethanolamine, aziridine, azetidine, pyrrolidine, piperidine, indoline, and isoindoline.

A method for producing the amine compound is not particularly limited, and a known method can be used as appropriate.

In addition, in the first step, the carbonyl compound represented by the general formula (2) and the amine compound represented by the general formula (3) are reacted with each other in the acidic solvent. The amount of the carbonyl compound used for the reaction is such that the concentration thereof in the acidic solvent is preferably 0.01 to 5.0 mol/L, and more preferably 0.1 to 2.0 mol/L. If the amount of the carbonyl compound is less than the lower limit, the production efficiency of the Mannich base represented by the general formula (4) tends to be lowered. Meanwhile, if the amount of the carbonyl compound exceeds the upper limit, a side-reaction product due to a side reaction tends to increase.

In addition, the amount of the amine compound used is preferably 2 equivalents or more, and more preferably 2 to 10 equivalents to the carbonyl compound. If the amount of the amine compound used is less than the lower limit, the yield of the Mannich base tends to be low. Meanwhile, if the amount of the amine compound used exceeds the upper limit, a side-reaction product due to a side reaction tends to increase.

In addition, the reaction conditions for reacting the carbonyl compound and the amine compound with each other in the acidic solvent are not particularly limited, and can be changed as appropriate depending on the kind of the solvent used, and the like. As for the reaction conditions, an atmosphere with which the acidic solvent is in contact is preferably an atmosphere of an inert gas such as nitrogen gas. In addition, from the viewpoint of promoting the reaction, the reaction is preferably allowed to proceed under heated conditions. As the heated conditions, conditions that the heating is conducted at a temperature of 30 to 180° C. (more preferably 80 to 120° C.) for 0.5 to 10 hours (more preferably 1 to 5 hours) are preferably employed. If the heating temperature and/or the heating time are less than the lower limit, the yield of the Mannich base represented by the general formula (4) tends to be low. Meanwhile, if the heating temperature and/or the heating time exceed the upper limit, by-products such as bis(vinyl ketone) and vinyl ketone dimer tend to increase, so that the yield of the Mannich base represented by the general formula (4) tends to be low.

By reacting the carbonyl compound represented by the general formula (2) and the amine compound represented by the general formula (3) with each other in the presence of the acidic solvent, it is possible to form the Mannich base represented by the following general formula (4):

[Chem. 16]

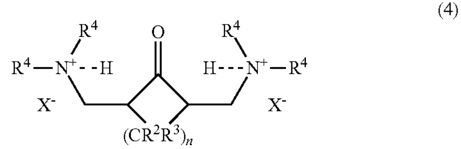

[$R^2$, $R^3$, and n in the formula (4) have the same meanings as those of $R^2$, $R^3$, and n in the formula (2), and $R^4$s and $X^-$ s in the formula (4) have the same meanings as those of $R^4$s and $X^-$ in the formula (3)]. Thus, the reaction liquid comprising the Mannich base in the acidic solvent can be obtained.

In addition, in the first step, by using the acidic solvent, the carbonyl compound and the amine compound are reacted with each other under an acidic condition where the acid (HX) is present in excess (under an acidic condition where 0.01 mol/L or more of the acid (HX) is present). This makes it possible to form the Mannich base represented by the general formula (4) in a sufficiently high yield. In this manner, the production efficiency and the yield of the reaction intermediate (the Mannich base) are sufficiently improved in the first step in the present invention. Then, in the present invention, the reaction liquid comprising the thus formed Mannich base is directly used in the second step. Hence, the Mannich base can be used efficiently. It is presumed that this aspect also leads to the improvement in the yield of the final target product.

(Second Step)

The second step is a step of reacting the Mannich base and a diene compound represented by the general formula (5) with each other by adding an organic solvent, a base in an amount of 1.0 to 20.0 equivalents to the acid, and the diene compound to the reaction liquid, and then heating the reaction liquid, to thereby form a bis(spiro norbornene) represented by the general formula (1).

In the second step, the reaction liquid obtained in the first step is used. In this manner, the Mannich base is not isolated in the present invention from the reaction liquid in the second step. Hence, the Mannich base, which is the reaction intermediate present in the reaction liquid, can be used highly efficiently, and the step can be simplified. Thus, the bis(spiro norbornene) can be produced sufficiently efficiently.

Moreover, in the second step, the organic solvent is added to the reaction liquid. The organic solvent is not particularly limited, and organic solvents which can be used for the so-called Diels-Alder reaction can be used as appropriate. Examples of the organic solvents include alcohol-based solvents (including glycol-based solvents, glycerin-based solvents, and other polyvalent alcohol-based solvents), cellosolve-based solvents, ether-based solvents, amide-based solvents, and nitrile-based solvents. A preferred organic solvent can be selected and used as appropriate depending on the kind of the target bis(spiro norbornene), and the like.

In addition, the organic solvent is preferably an organic solvent immiscible with a saturated hydrocarbon having 5 to 30 carbon atoms, from the viewpoint of simplifying an extraction step which follows the reaction. As the organic solvent immiscible with a saturated hydrocarbon having 5 to 30 carbon atoms, methanol, methyl cellosolve, dimethylacetamide, dimethyl sulfoxide, ethylene glycol, propylene glycol, 1,3-propanediol, glycerin, propylene glycol monomethyl ether, ethyl cellosolve, dimethylformamide, acetonitrile, or the like is preferable. Of these organic solvents, methanol or methyl cellosolve is more preferable from the viewpoint of ease and convenience of extraction operations.

In addition, the amount of the organic solvent added to the reaction liquid is not particularly limited, and is preferably 10 to 80% by mass (more preferably 20 to 60% by mass) relative to the total amount of the reaction liquid and the organic solvent added. If the amount of the organic solvent added is less than the lower limit, the reaction rate tends to be low, and hence the yield tends to decrease. Meanwhile, if the amount of the organic solvent added exceeds the upper limit, by-products such as vinyl ketone dimer tend to increase, so that the yield of the target product tends to be low.

In addition, the base is added to the reaction liquid in the second step. The kind of the base is not particularly limited, and amines, alkali metal hydroxides, and alkaline earth metal hydroxides can be used preferably, from the viewpoint of basicity. Of these bases, dimethylamine, diethylamine, dipropylamine, and dibutylamine are preferable, and dimethylamine is particularly preferable, from the viewpoint of purification.

In addition, the amount of the base added needs to be 1.0 to 20.0 equivalents (more preferably 1.0 to 10.0 equivalents, and further preferably 1.0 to 5.0 equivalents) to the acid comprised in the reaction liquid. If the amount of the base added is less than the lower limit, the degradation of the Mannich base is suppressed, so that the bis(vinyl ketone) intermediate, which serves as a raw material of the target product, is not produced. Meanwhile, if the amount of the base added exceeds the upper limit, the extraction becomes difficult because a large amount of a neutralizing agent is necessary during the purification. As describe above, in the present invention, with the reaction liquid being made neutral or basic, the Mannich base and a diene compound are reacted with each other in the second step. Thus, the formation of by-products (for example, a dimerization product (dimer) formed due to dimerization by the hetero Diels-Alder reaction of a bis(vinyl ketone) formed by elimination of an amino compound from the Mannich base) is sufficiently suppressed, so that the target bis(spiro norbornene) can be produced in a sufficiently high selectivity.

Moreover, in the second step, a diene compound represented by the following general formula (5) is added to the reaction liquid:

[Chem. 17]

(5)

[in the formula (5), $R^1$ represents at least one selected from the group consisting of a hydrogen atom, alkyl groups having 1 to 10 carbon atoms, and a fluorine atom].

The substituents which can be selected as $R^1$ in the general formula (5) are the same as the substituents which can be selected as each $R^1$ in the general formula (1), and preferred examples thereof are also the same.

The amount of the diene compound added is preferably 2 equivalents or more, and more preferably 2 to 10 equivalents, to the Mannich base represented by the general formula (4). If the amount of the diene compound added is less than the lower limit, the yield of the bis(spiro norbornene) tends to be low. Meanwhile, if the amount of the diene compound added exceeds the upper limit, a by-product due to a side reaction tends to increase.

In addition, in the second step, after the organic solvent, the base, and the diene compound are added to the reaction liquid, the Mannich base and a diene compound are reacted with each other by heating the obtained mixture liquid.

Any conditions can be employed for the heating, as long as the bis(spiro norbornene) represented by the general formula (1) can be produced by reacting the Mannich base and the diene compound with each other in the mixture liquid. A heating temperature for reacting the Mannich base and the diene compound with each other is preferably 30 to 180° C. (more preferably 80 to 140° C.). If the heating temperature is lower than the lower limit, the degradation rate of the Mannich base tends to be low, so that the yield of the target product tends to decrease. Meanwhile, if the heating temperature exceeds the upper limit, by-products such as vinyl ketone dimer and tetracyclododecene which is formed by a Diels-Alder addition of another molecule of the diene to the target product tend to increase, so that the selectivity for the target product tends to be low.

In addition, a hearting time for reacting the Mannich base and the diene compound with each other is preferably 0.01 to 5.0 hours, and more preferably 0.1 to 1.5 hours. If the hearting time is less than the lower limit, the yield tends to be low. Meanwhile, if the hearting time exceeds the upper limit, by-products tend to increase. Note that an atmosphere during the heating is preferably an atmosphere of an inert gas such as nitrogen gas, from the viewpoints of coloring-prevention and safety.

In addition, as a method for the heating, it is possible to employ a method in which a mixture liquid of the Mannich base, the diene compound, the base, and the organic solvent is added dropwise to a reaction vessel preheated to the heating temperature. In addition, when the method in which the mixture liquid is added dropwise as described above is employed, a portion of the organic solvent may be placed in the reaction vessel in advance. This enables the reaction to proceed more safely.

In addition, when an organic solvent having a boiling point lower than the heating temperature is used, a pressure container such as an autoclave may be employed. In this case, the heating may be started at normal pressure, or at a predetermined pressure. This allows various kinds of organic solvents to be used, and also enables reduction in thermal energy for solvent recycling.

By adding the organic solvent, the base, and the diene compound to the reaction liquid, and then heating the mixture liquid as described above, the 5-norbornene-2-spiro-α-cycloalkanone-α'-spiro-2"-5"-norbornene represented by the general formula (1) can be obtained. Note that, when the bis(spiro norbornene) is obtained, first, an amine compound is eliminated from the Mannich base represented by the general formula (4) under a neutral or basic condition by heating a mixture liquid obtained by adding the organic solvent, the base, and the diene compound to the reaction liquid, so that a compound having a bis(vinyl ketone) structure represented by the following general formula (6) is formed:

[Chem. 18]

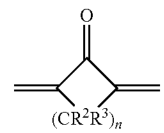

(6)

[in the formula (6), $R^2$, $R^3$, and n have the same meanings as those of $R^2$, $R^3$, and n in the formula (2)]. Subsequently, the compound having the bis(vinyl ketone) structure and the diene compound represented by the general formula (5) are reacted with each other by the so-called Diels-Alder reaction, so that the bis(spiro norbornene) represented by the general formula (1) is formed. In the present invention, the reaction is allowed to proceed under a neutral or basic condition as described above. Hence, the formation of by-products can be suppressed at a higher level, and the bis(spiro norbornene) can be produced more efficiently.

In addition, after the formation of the bis(spiro norbornene) by the reaction, the percentage of the compound having the bis(vinyl ketone) structure present in the mixture liquid after the reaction is preferably 2 mol % or less relative to the bis(spiro norbornene) (the target product). If the percentage of the compound having the bis(vinyl ketone) structure present exceeds the upper limit, the target product tends to be colored, or a product tends to be viscous due to dimerization. Note that, from the viewpoint that the percentage of the compound having the bis(vinyl ketone) structure present is more surely made 2 mol % or less, it is preferable to make the content of the base 2.0 to 5.0 equivalents to the acid comprised in the reaction liquid, and the heating temperature 50 to 125° C., and the hearting time 0.5 to 10 hours, in the second step.

In addition, after the formation of the bis(spiro norbornene) by the reaction, the percentage of the dimerization product (dimer), which is formed by dimerization of the compound having the bis(vinyl ketone) structure, present in the mixture liquid after the reaction is preferably 2 mol % or less relative to the bis(spiro norbornene) (the target product). If the percentage of the dimmer present exceeds the upper limit, a product tends to be viscous. Note that, from the viewpoint that the percentage of the dimmer present is more surely made 2 mol % or less, it is preferable to make the content of the base 2.0 to 5.0 equivalents to the acid comprised in the reaction liquid, the heating temperature 50 to 125° C., and the hearting time 0.5 to 10 hours, in the second step. Note that the percentages of the compound having the bis(vinyl ketone) structure and the dimer which are present in the mixture liquid can be measured by the so-called HPLC analysis. As the apparatus used for the HPLC analysis and the like, a known apparatus and the like can be used as appropriate.

In addition, a method for extracting, after the formation of the bis(spiro norbornene) by the reaction, the bis(spiro norbornene) from the mixture liquid after the reaction is not particularly limited, and a known method may be employed as appropriate. In addition, as the extraction method, it is preferable to employ a method in which the solvent is removed from the mixture liquid in which the bis(spiro norbornene) is formed, and then, while an obtained mixture is used as it is, or with water added thereto as appropriate, the bis(spiro norbornene) is separated by extraction with a saturated hydrocarbon having 5 to 30 (more preferably 5 to 10) carbon atoms. By extracting the bis(spiro norbornene) by use of such a saturated hydrocarbon, by-products such as amine salts and heavy products can be removed easily and conveniently. In addition, when water is added to the mixture in the step, the amount of water added is not particularly limited, and may be changed as appropriate depending on the amount of the mixture to be obtained, the apparatus used for the extraction, and the like. Note that the solvent removed from the mixture liquid in the method of the separation by extraction is the organic solvent added to the reaction liquid, which may be, for example, an organic solvent miscible with the saturated hydrocarbon having 5 to 30 carbon atoms.

Moreover, in the present invention, from the viewpoint of separating the bis(spiro norbornene) by extraction more efficiently, it is preferable to employ a method in which the bis(spiro norbornene) is formed by using an organic solvent immiscible with a saturated hydrocarbon having 5 to 30 carbon atoms as the organic solvent added to the reaction liquid, and after that the bis(spiro norbornene) is separated by liquid-liquid extraction by using a saturated hydrocarbon having 5 to 30 (more preferably 5 to 20, and further preferably 5 to 10) carbon atoms in the mixture liquid after the reaction. Note that the method for isolating and purifying the bis(spiro norbornene) after the extraction liquid is obtained by separating the bis(spiro norbornene) by extraction as described above is not particularly limited, and a known method can be employed as appropriate.

In addition, in the present invention, it is preferable to further comprise, after the step of separation by extraction, a step of washing, with an aqueous alkali solution and an aqueous acid solution, an extraction liquid which is obtained by separating the bis(spiro norbornene) by extraction with the saturated hydrocarbon having 5 to 30 carbon atoms, and which comprises the bis(spiro norbornene) and the saturated hydrocarbon. In the washing treatment, it is desirable to wash the extraction liquid with an aqueous alkali solution comprising an amine, an alkali metal hydroxide, an alkaline earth metal hydroxide, or the like, and subsequently with an aqueous acid solution comprising an inorganic acid, an organic acid, or the like, thereafter to neutralize the extraction liquid with weakly alkaline or weakly acidic water, and to dehydrate the extraction liquid with a dehydrating agent such as saturated aqueous sodium chloride.

As the aqueous alkali solution, aqueous ammonia, aqueous sodium hydroxide, aqueous potassium hydroxide, aqueous calcium hydroxide, or the like is preferable, and aqueous sodium hydroxide is particularly preferable. In addition, the concentration of the alkali component in the aqueous alkali solution is preferably about 1 to 20% by mass. By washing the extraction liquid comprising the bis(spiro norbornene) by use of such an aqueous alkali solution, by-products such as amine salts and heavy products can be removed easily and conveniently.

Meanwhile, as the aqueous acid solution, aqueous hydrochloric acid, aqueous sulfuric acid, aqueous phosphoric acid, aqueous nitric acid, aqueous acetic acid, or the like is preferable, and aqueous hydrochloric acid is particularly preferable. In addition, the concentration of the acid in the aqueous acid solution is preferably about 1 to 20% by mass. By washing the extraction liquid comprising the bis(spiro norbornene) by use of such an aqueous acid solution, by-products such as amine salts and heavy products can be removed easily and conveniently.

Regarding the order of the washings, the washing with the aqueous acid solution may be conducted before the washing with the aqueous alkali solution. In addition, as the weakly alkaline water used for the neutralization in the washing treatment, aqueous sodium carbonate, aqueous sodium hydrogen carbonate, aqueous potassium carbonate, aqueous sodium acetate, or the like is preferable, and aqueous sodium hydrogen carbonate is particularly preferable. The use of the weakly alkaline water enables the pH of the liquid to be made around neutral in a short period of time, and also enables degradation to be suppressed during the subsequent distillation purification. In addition, as the weakly acidic water used for the neutralization in the washing treatment, aqueous ammonium chloride, aqueous ammonium sulfate, aqueous ammonium nitrate, aqueous ammonium phosphate, or the like is preferable, and aqueous ammonium chloride is particularly preferable. The use of the weakly acidic water enables the pH of the liquid to be made around neutral in a short period of time, and also enables degradation to be suppressed during the subsequent distillation purification.

In addition, as the dehydrating agent used in the washing treatment, saturated aqueous sodium chloride, anhydrous magnesium sulfate, anhydrous sodium sulfate, silica gel, calcium oxide, diphosphorus pentoxide, or the like is preferable, and saturated aqueous sodium chloride or anhydrous magnesium sulfate is particularly preferable. Moreover, azeotropic dehydration with addition of benzene, toluene, or the like can be employed. By dehydrating the extraction liquid comprising the bis(spiro norbornene) by use of the dehydrating agent, the water in the liquid can be reduced, and separation of water can be suppressed during subsequent concentration of the extraction liquid. According to the method for producing a 5-norbornene-2-spiro-α-cycloalkanone-α'-spiro-2"-5"-norbornene of the present invention, the bis(spiro norbornene) represented by the general formula (1) can be produced in a sufficient yield. In addition, according to the method for producing a 5-norbornene-2-spiro-α-cycloalkanone-α'-spiro-2"-5"-norbornene of the present invention, the endo/exo ratio of the configuration of substituents in the bis(spiro norbornene) represented by the general formula (1) can be made 10/90 to 30/70 (more preferably 15/85 to 25/75). In the present invention, the bis(spiro norbornene) is produced in the second step by degrading the Mannich base, and simultaneously causing a Diels-Alder reaction. Here, when the heating temperature (reaction temperature) in the second step is set within the above-described preferred range (for example, 30 to 180° C.), the variable endo/exo ratio naturally falls in the above-described range. Note that the bis(spiro norbornene) of the present invention has a ketone group, and the ketone group has priority in nomenclature. Hence, although the bis(spiro norbornene) is an endo adduct from the viewpoint of the reaction, the bis(spiro norbornene) obtained by the reaction is an exo isomer from the viewpoint of nomenclature.

In addition, the bis(spiro norbornene) represented by the general formula (1) obtained as described above is preferable as a raw material for an acid dianhydride monomer for polyimides. Colorless transparent polyimides obtained by using the bis(spiro norbornene) as a starting raw material are particularly useful as materials for producing films for flexible printed wiring boards, heat resistant insulating tapes, enamels for wires, protective coating agents for semiconductors, liquid crystal orientation films, transparent electro-conductive films for organic ELs, flexible substrate films, flexible transparent electro-conductive films, transparent electro-conductive films for organic thin-film solar cells, transparent electro-conductive films for dye-sensitized solar cells, flexible gas-barrier films, films for touch panels, and the like. Furthermore, the bis(spiro norbornene) can be converted into a desired polymer or a cross-linked product, by subjecting the bis(spiro norbornene) alone to a metathesis reaction, an addition polymerization, a radical polymerization, a cationic polymerization, an anionic polymerization, or the like. Moreover, if necessary, it is also possible to obtain a copolymer or a copolymerization cross-linked product by subjecting the bis(spiro norbornene) to a copolymerization reaction with any copolymerizable compound. In addition, an acid dianhydride obtained from the bis(spiro norbornene) is useful not only as a monomer for polyimides, but also as an epoxy-curing agent and a raw material for maleimides.

In addition, a method for producing an acid dianhydride, which is preferable as a raw material compound of polyimides, by use of the bis(spiro norbornene) is not particularly limited, and a known method can be used as appropriate. For example, the method described on Page 1117 of Macromolecules (vol. 27) published in 1994 may be utilized.

EXAMPLES

Hereinafter, the present invention will be described more specifically based on Examples and Comparative Example. However, the present invention is not limited to Examples below.

Note that, in the following description, the molecule structure of the compound obtained in each Example was identified by measuring IR and NMR spectra by use of IR measuring apparatuses (manufactured by JASCO Corporation, trade name: FT/IR-460 and FT/IR-4100) and NMR measuring apparatuses (manufactured by VARIAN, trade name: UNITY INOVA-600 and manufactured by JEOL Ltd., JNM-Lambda500). In addition, glass transition temperatures (Tg) shown in Test Examples were measured by using a DSC 7020 differential scanning calorimeter manufactured by SII NanoTechnology Inc.

Example 1

<First Step>

First, to a 100-ml two-necked flask, 6.83 g of a 50% by mass aqueous dimethylamine solution (dimethylamine: 75.9 mmol) was added. Next, to a 100-ml dropping funnel, 8.19 g of a 35% by mass aqueous solution of hydrochloric acid (hydrogen chloride: 78.9 mmol) was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde and 2.59 g (30.8 mmol) of cyclopentanone were further added. Subsequently, a bulb condenser was set to the two-necked flask, and then the inside of the two-necked flask was replaced with nitrogen. After that, the two-necked flask was immersed in an oil bath of 90° C., and heated for 3 hours with stirring. Thus, a reaction liquid was obtained which contained a Mannich base which was a compound represented by the general formula (4), in which n was 2, $R^2$ and $R^3$ were all hydrogen atoms, and $R^4$s were each a methyl group. Note that the thus obtained reaction liquid was subjected to gas chromatography analysis (GC analysis: a detector manufactured by Agilent Technologies under the trade name of “6890N” was used). As a result, it was found that the conversion of cyclopentanone was 99%.

<Second Step>

Next, the reaction liquid in the two-necked flask was cooled to 50° C. Then, to the reaction liquid in the two-necked flask, methyl cellosolve (50 ml), 1.12 g (12.4 mmol) of a 50% by mass aqueous dimethylamine solution, and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 90 minutes.

<Extraction Treatment>

The mixture liquid after heating was cooled to room temperature (25° C.), and then transferred to a 200-ml separatory funnel. Then, a first extraction operation was conducted by adding n-heptane (80 ml) thereto, and recovering a n-heptane layer. Next, a second extraction operation was conducted by adding n-heptane (40 ml) to the remaining methyl cellosolve layer, and recovering a n-heptane layer. Then, the n-heptane layers obtained by the first and second extraction operations were mixed with each other. Thus, a n-heptane extraction liquid was obtained.

Next, the n-heptane extraction liquid was washed once with 5% by mass aqueous NaOH (25 ml), and then washed once with 5% by mass aqueous hydrochloric acid (25 ml). Subsequently, the n-heptane extraction liquid washed with the aqueous hydrochloric acid was washed once with 5% by mass aqueous sodium hydrogen carbonate (25 ml), and further once with saturated aqueous sodium chloride (25 ml). Subsequently, the thus washed n-heptane extraction liquid was dried over anhydrous magnesium sulfate, and then the anhydrous magnesium sulfate was filtered off. Thus, a filtrate was obtained. Subsequently, the obtained filtrate was concentrated by using an evaporator, and n-heptane was evaporated. Thus, 7.4 g of a crude product (5-norbornene-2-spiro-2'-cyclopentanone-5'-spiro-2"-5"-norbornene) was obtained (yield of crude: 99%). Next, the thus obtained crude product was subjected to Kugelrohr distillation (boiling point: 105° C./0.1 mmHg), and 4.5 g of 5-norbornene-2-spiro-2'-cyclopentanone-5'-spiro-2"-5"-norbornene was obtained (yield: 61%).

Figure 2:
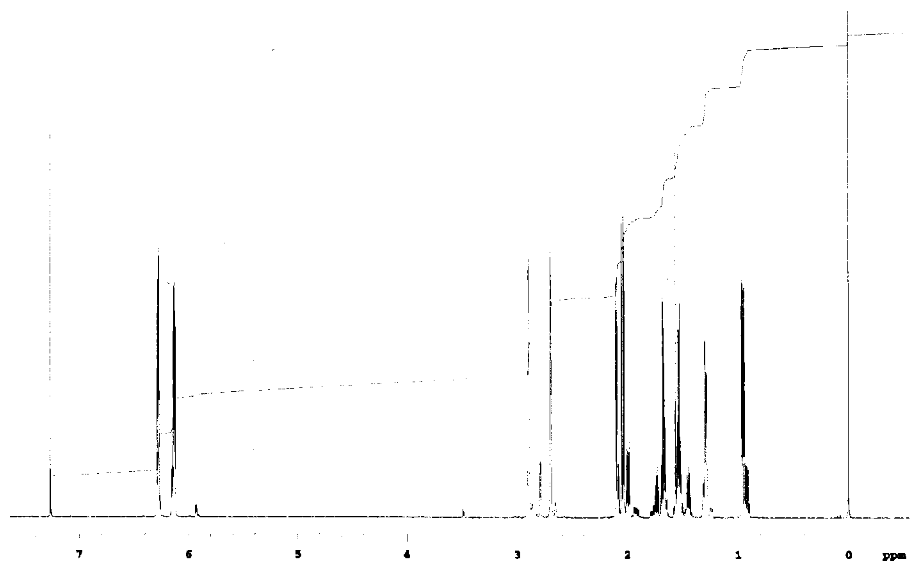
FIG. 2 is a graph showing a $^{1}$H-NMR ($CDCl_3$) spectrum of the 5-norbornene-2-spiro-2'-cyclopentanone-5'-spiro-2"-5"-norbornene obtained in Example 1.
Figure 3:
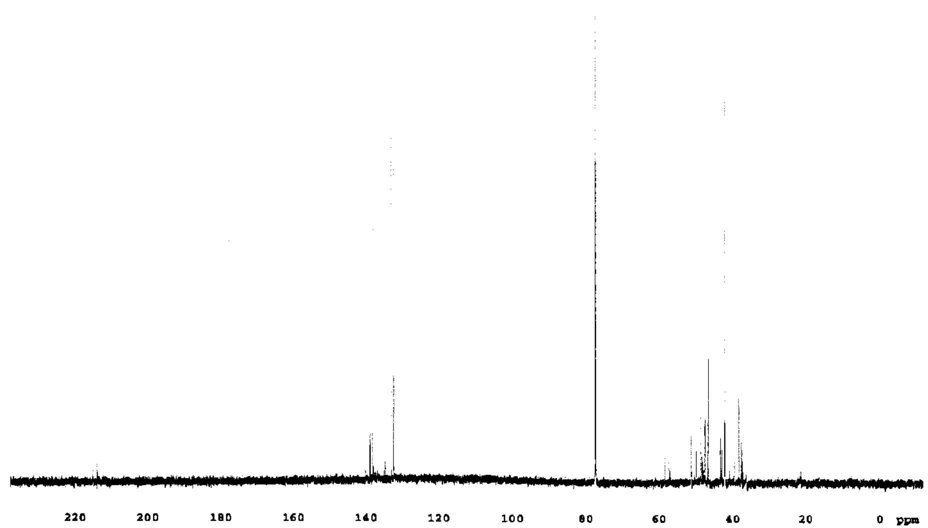
FIG. 3 is a graph showing a $^{13}$C-NMR ($CDCl_3$) spectrum of the 5-norbornene-2-spiro-2'-cyclopentanone-5'-spiro-2"-5"-norbornene obtained in Example 1.

To confirm the structure of the thus obtained compound, IR and NMR ($^1$H-NMR and $^{13}$C-NMR) measurements were conducted. FIG. 1 shows an IR spectrum of the thus obtained compound, FIG. 2 shows a $^1$H-NMR ($CDCl_3$) spectrum thereof, and FIG. 3 shows a $^{13}$C-NMR ($CDCl_3$) spectrum thereof. From the results shown in FIGS. 1 to 3, the obtained compound was confirmed to be 5-norbornene-2-spiro-2'-cyclopentanone-5'-spiro-2"-5"-norbornene represented by the following general formula (7):

[Chem. 19]

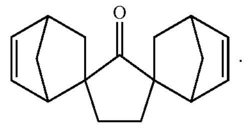

(7)

In addition, from the results shown in FIGS. 1 to 3, it was found that the ratio (endo/exo) between the endo isomer and the exo isomer was 10/90 in the 5-norbornene-2-spiro-2'-cyclopentanone-5'-spiro-2"-5"-norbornene.

Example 2

<First Step>

First, to a 100-ml two-necked flask, 6.83 g of a 50% by mass aqueous dimethylamine solution (dimethylamine: 75.9 mmol) was added. Next, to 100-ml dropping funnel, 8.19 g of a 35% by mass aqueous solution of hydrochloric acid (hydrogen chloride: 78.9 mmol) was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde and 3.02 g (30.8 mmol) of cyclohexanone were further added. Subsequently, a bulb condenser was set to the two-necked flask, and the inside of the two-necked flask was replaced with nitrogen. Thereafter, the two-necked flask was immersed in an oil bath of 90° C., and heated for 4 hours with stirring. Thus, a reaction liquid was obtained which contained a Mannich base which was a compound represented by the general formula (4), in which n was 2, $R^2$ and $R^3$ were all hydrogen atoms, and $R^4$s were each a methyl group. Note that the thus obtained reaction liquid was subjected to a GC analysis in the same manner as in Example 1. As a result, it was found that the conversion of cyclohexanone was 99%.

<Second Step>

Next, the reaction liquid in the two-necked flask was cooled to 50° C. Then, to the reaction liquid, methyl cellosolve (50 ml), 1.12 g (12.4 mmol) of a 50% by mass aqueous dimethylamine solution, and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 90 minutes.

<Extraction Treatment>

The mixture liquid after heating was cooled to room temperature (25° C.), and then transferred to a 200-ml separatory funnel. Then, a first extraction operation was conducted by adding n-heptane (80 ml), and then recovering a n-heptane layer. Next, a second extraction operation was conducted by adding n-heptane (40 ml) to the remaining methyl cellosolve layer and recovering a n-heptane layer. Then, the n-heptane layers obtained by the first and second extraction operations were mixed with each other. Thus, a n-heptane extraction liquid was obtained.

Next, the n-heptane extraction liquid was washed once with 5% by mass aqueous NaOH (25 ml), and then once with 5% by mass aqueous hydrochloric acid (25 ml). Subsequently, the n-heptane extraction liquid washed with the aqueous hydrochloric acid was washed once with 5% by mass aqueous sodium hydrogen carbonate (25 ml), and further once with saturated aqueous sodium chloride (25 ml). Subsequently, the thus washed n-heptane extraction liquid was dried over anhydrous magnesium sulfate, and then the anhydrous magnesium sulfate was filtered off. Thus, a filtrate was obtained. Subsequently, the obtained filtrate was concentrated by using an evaporator, and n-heptane was evaporated. Thus, 7.8 g of a crude product (5-norbornene-2-spiro-2'-cyclohexanone-6'-spiro-2"-5"-norbornene) was obtained (yield of crude: 99%). Next, the thus obtained crude product was subjected to Kugelrohr distillation (boiling point: 120 to 145° C./0.1 mmHg), and 4.4 g of 5-norbornene-2-spiro-2'-cyclohexanone-6'-spiro-2"-5"-norbornene was obtained (yield: 56%).

Figure 4:
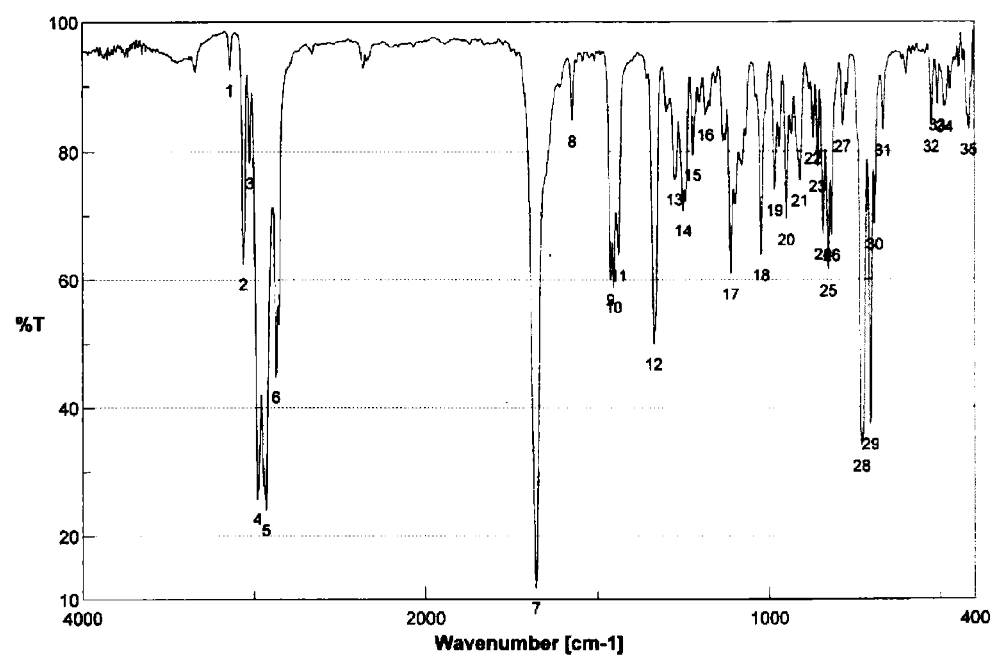
FIG. 4 is a graph showing an IR spectrum of 5-norbornene-2-spiro-2'-cyclohexanone-6'-Spiro-2"-5"-norbornene obtained in Example 2.
Figure 5:
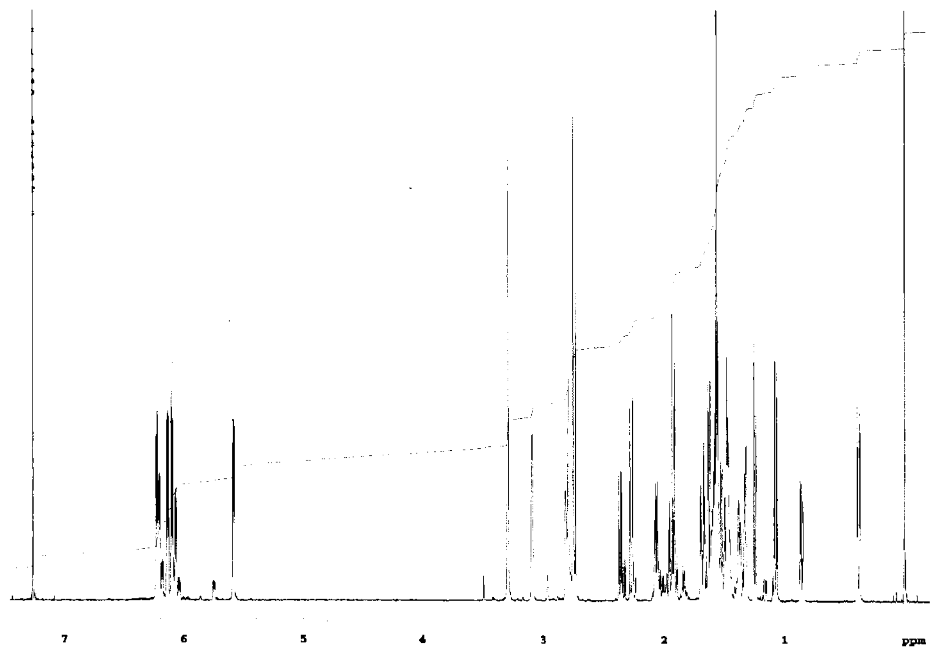
FIG. 5 is a graph showing a $^{1}$H-NMR($CDCl_3$) spectrum of the 5-norbornene-2-spiro-2'-cyclohexanone-6'-spiro-2"-5"-norbornene obtained in Example 2.
Figure 6:
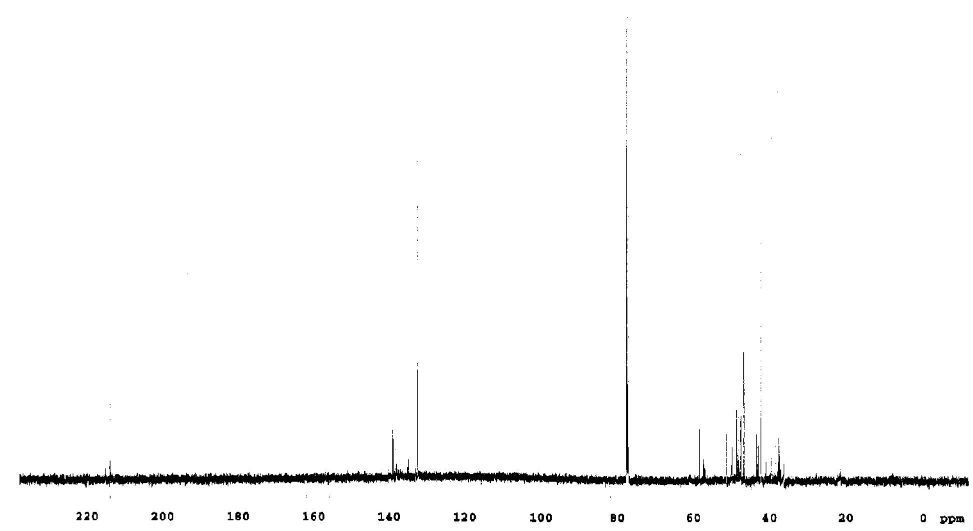
FIG. 6 is a graph showing a $^{13}$C-NMR($CDCl_3$) spectrum of the 5-norbornene-2-spiro-2'-cyclohexanone-6'-spiro-2"-5"-norbornene obtained in Example 2.

To confirm the structure of the thus obtained compound, IR and NMR ($^1$H-NMR and $^{13}$C-NMR) measurements were conducted. FIG. 4 shows an IR spectrum of the thus obtained compound, FIG. 5 shows a $^1$H-NMR ($CDCl_3$) spectrum thereof, and FIG. 6 shows a $^{13}$C-NMR ($CDCl_3$) spectrum thereof. From the results shown in FIGS. 4 to 6, the obtained compound was confirmed to be 5-norbornene-2-spiro-2'-cyclohexanone-6'-spiro-2"-5"-norbornene represented by the following general formula (8):

[Chem. 20]

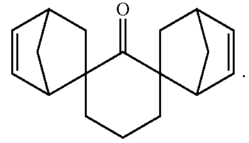

(8)

In addition, it was found that cis and trans isomers of the spiro condensation ring had an endo isomer and an exo isomer, in the 5-norbornene-2-spiro-2'-cyclohexanone-6'-spiro-2"-5"-norbornene, and it was found based on the number of olefins that the 5-norbornene-2-spiro-2'-cyclohexanone-6'-spiro-2"-5"-norbornene was a mixture of six isomers.

Test Example 1

Polyimide Preparation

A tetracarboxylic dianhydride was produced according to the method described on page 1117 of Macromolecules (vol. 27) published in 1994 by use of the 5-norbornene-2-spiro-2'-cyclopentanone-5'-spiro-2"-5"-norbornene obtained in Example 1. As a result of the production of the tetracarboxylic dianhydride in this manner, norbornane-2-spiro-α-cyclopentanone-α'-spiro-2"-norbornane-5,5",6,6"-tetracarboxylic dianhydride was obtained in a total yield of 88%.

Next, a 30-ml three-necked flask was dried by heating with a heat gun. Then, to the sufficiently dried three-necked flask, first, 0.200 g (1.00 mmol) of 4,4'-diaminodiphenyl ether (solid) was introduced, and then 2.7 g of dimethylacetamide was added. The solid was dissolved with stirring. Thus, a solution was obtained. Subsequently, 0.384 g (1.00 mmol) of the norbornane-2-spiro-α-cyclopentanone-α'-spiro-2"-norbornane-5,5",6,6"-tetracarboxylic dianhydride obtained as described above was added to the solution. The atmosphere inside the three-necked flask was replaced with a nitrogen atmosphere, followed by stirring under a nitrogen atmosphere at room temperature (25° C.) for 22 hours. Thus, a reaction liquid was obtained.

Subsequently, the reaction liquid was cast on a glass plate to form a coating on the glass plate. Then, the glass plate on which the coating was formed was introduced into a vacuum oven, and the coating was cured by heating under a pressure of 1 mmHg at 80° C. for 1 hour, 170° C. for 1 hour, and 250° C. for 1 hour, in this order. Thus, a film was formed on the glass plate. Then, the glass plate on which the film was formed was taken out of the vacuum oven, and the film was recovered from the glass plate by immersing the glass plate in hot water of 70° C. An IR spectrum of the thus obtained film was measured. As a result, C=O stretching vibration of imidocarbonyl was observed at 1778 and 1709 $cm^{-1}$. Hence, the obtained film was confirmed to be made of a polyimide. Note that an outline of the reaction in the production process of the polyimide is shown in the following reaction formula (III):

[Chem. 21]

[Reaction Formula (III)]

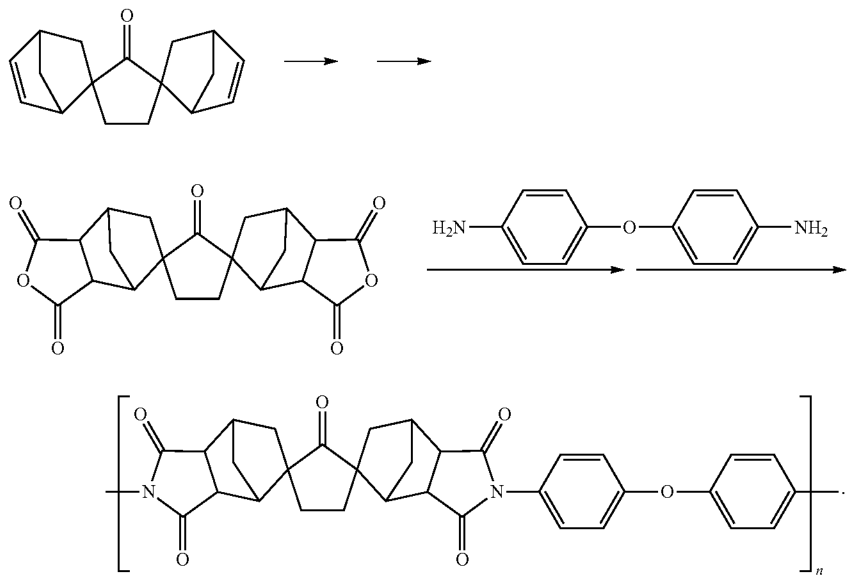

Differential scanning calorimetry (DSC) was conducted on the thus obtained film-shaped polyimide. As a result, no glass transition temperature Tg was observed from room temperature to 420° C., and it was found that the glass transition temperature Tg of the obtained polyimide exceeded 420° C. From the result of the thermal analysis, it was found that the polyimide produced from the bis(spiro norbornene) obtained in Example 1 had a sufficiently high level of heat resistance. In addition, it was found that the film was colorless and transparent, and exhibited a sufficiently high light transmittance.

Test Example 2

Polyimide Preparation

A tetracarboxylic dianhydride was produced according to the method described on Page 1117 of Macromolecules (vol. 27) published in 1994 by use of the 5-norbornene-2-spiro-2'-cyclohexanone-6'-spiro-2"-5"-norbornene obtained in Example 2. As a result of the production of the tetracarboxylic dianhydride in this manner, norbornane-2-spiro-α-cyclohexanone-α'-spiro-2"-norbornane-5,5",6,6"-tetracarboxylic dianhydride was obtained in a total yield of 87%.

Next, a 30-ml three-necked flask was dried by heating with a heat gun. Then, to the sufficiently dried three-necked flask, first, 0.200 g (1.00 mmol) of 4,4'-diaminodiphenyl ether (solid) was introduced, and then 2.7 g of dimethylacetamide was added. The solid was dissolved with stirring. Thus, a solution was obtained. Subsequently, 0.398 g (1.00 mmol) of the norbornane-2-spiro-α-cyclohexanone-α'-spiro-2"-norbornane-5,5",6,6"-tetracarboxylic dianhydride obtained as described above was added to the solution. The atmosphere inside the three-necked flask was replaced with a nitrogen atmosphere, followed by stirring under a nitrogen atmosphere at room temperature (25° C.) for 22 hours. Thus, a reaction liquid was obtained.

Subsequently, the reaction liquid was cast on a glass plate to form a coating on the glass plate. Then, the glass plate on which the coating was formed was introduced into a vacuum oven, and the coating was cured by heating under a pressure of 1 mmHg at 80° C. for 1 hour, 170° C. for 1 hour, and 250° C. for 1 hour, in this order. Thus, a film was formed on the glass plate. Then, the glass plate on which the film was formed was taken out of the vacuum oven, and the film was recovered from the glass plate by immersing the glass plate in hot water of 70° C. An IR spectrum of the thus obtained film was measured. As a result, C═O stretching vibration of imidocarbonyl was observed at 1779 and 1702 $cm^{-1}$. Hence, the obtained film was confirmed to be made of a polyimide. Note that an outline of the reaction in the production process of the polyimide is shown in the following reaction formula (IV):

[Chem. 22]

[Reaction Formula (IV)]

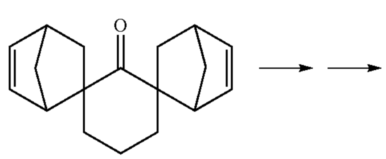

-continued

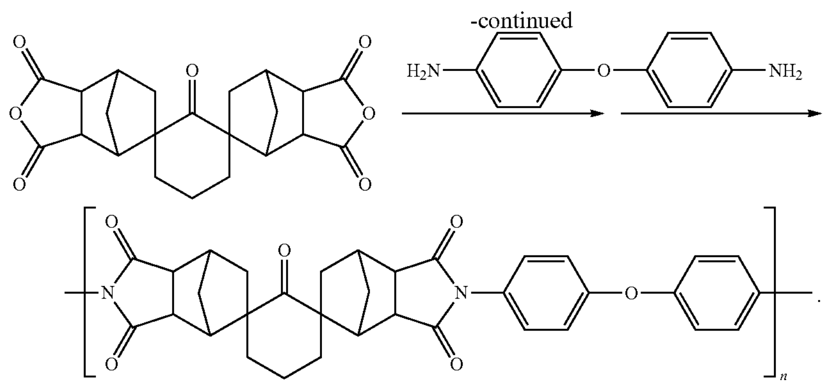

Differential scanning calorimetry (DSC) was conducted on the thus obtained film-shaped polyimide. As a result, no glass transition temperature Tg was observed from room temperature to 420° C., and it was found that the glass transition temperature Tg of the obtained polyimide exceeded 420° C. From the results of the thermal analysis, it was found that the polyimide derived from the bis(spiro norbornene) obtained in Example 2 had a sufficiently high level of heat resistance. In addition, it was found that the film was colorless and transparent, and exhibited a sufficiently high light transmittance.

[Industrial Applicability]

As described above, according to the present invention, it is possible to provide a 5-norbornene-2-spiro-α-cycloalkanone-α'-spiro-2"-5"-norbornene which can be preferably used as a raw material compound of an alicyclic tetracarboxylic dianhydride used for producing an alicyclic polyimide having a high light transmittance and a sufficiently high level of heat resistance; and a method for producing a 5-norbornene-2-spiro-α-cycloalkanone-α'-spiro-2"-5"-norbornene, the method making it possible to efficiently produce a 5-norbornene-2-spiro-α-cycloalkanone-α'-spiro-2"-5"-norbornene in a sufficiently high yield.

In addition, the 5-norbornene-2-spiro-α-cycloalkanone-α'-spiro-2"-5"-norbornene of the present invention enables a polyimide obtained by using the same to have a sufficiently high level of heat resistance with a glass transition temperature comparable to that of the wholly aromatic polyimide (trade name "Kapton": glass transition temperature 410° C.), even though the polyimide is an alicyclic polyimide. Hence, the 5-norbornene-2-spiro-α-cycloalkanone-α'-spiro-2"-5"-norbornene of the present invention is particularly useful as a raw material compound (raw material monomer) for producing polyimides for flexible printed wiring boards, polyimides for heat resistant insulating tapes, polyimides for enamels for wires, polyimides for protective coatings of semiconductors, polyimides for liquid crystal orientation films, polyimides for transparent electrode substrates of organic ELs, polyimides for transparent electrode substrates of solar cells, polyimides for transparent electrode substrates of electronic papers, materials for various substrates of gas-barrier films, and the like, where an extremely high level of heat resistance is required; and as the like.

The invention claimed is:

1. A 5-norbornene-2-spiro-α-cycloalkanone-α'-spiro-2"-5"-norbornene represented by the following general formula (1):

(1)

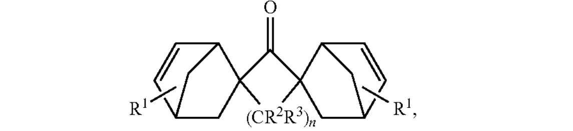

wherein in the formula (1), $R^1$s, $R^2$, and $R^3$ each independently represent one selected from the group consisting of a hydrogen atom, alkyl groups having 1 to 10 carbon atoms, and a fluorine atom, and n represents an integer of 0 to 12.

2. A method for producing a 5-norbornene-2-spiro-α-cycloalkanone-α'-spiro-2"-5"-norbornene, comprising:

a first step of forming a Mannich base by reacting a carbonyl compound and an amine compound with each other in an acidic solvent, to thereby obtain a reaction liquid comprising the Mannich base in the acidic solvent, the acidic solvent comprising a formaldehyde derivative and 0.01 mol/L or more of an acid represented by a formula: HX, wherein, in the formula, X represents one selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$, the carbonyl compound being represented by the following general formula (2):

(2)

O $(CR^2R^3)_n$, wherein in the formula (2), $R^2$ and $R^3$ each independently represent one selected from the group consisting of a hydrogen atom, alkyl groups having 1 to 10 carbon atoms, and a fluorine atom, and n represents an integer of 0 to 12, the amine compound being represented by the following general formula (3):

(3)

$$R^4R^4N^+H\cdots H,\ X^-$$

wherein in the formula (3), $R^4$s each independently represent one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, and saturated hydrocarbon groups having a hydroxyl group and 1 to 10 carbon atoms, provided that the two $R^4$s may be bonded to each other to form a ring selected from the group consisting of a pyrrolidine ring, a piperidine ring, a piperazine ring, and a morpholine ring, and $X^-$ represents one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$, the Mannich base being represented by the following general formula (4):

(4)

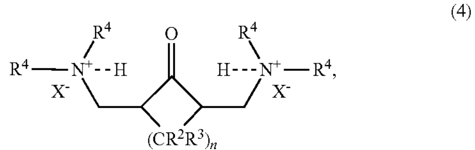

wherein $R^2$, $R^3$, and n in the formula (4) have the same meanings as those of $R^2$, $R^3$, and n in the formula (2), and $R^4$s and $X^-$s in the formula (4) have the same meanings as those of $R^4$s and $X^-$ in the formula (3); and a second step of reacting the Mannich base and a diene compound with each other by adding an organic solvent, a base in an amount of 1.0 to 20.0 equivalents to the acid, and the diene compound to the reaction liquid, and then heating the reaction liquid, to thereby form a 5-norbornene-2-spiro-α-cycloalkanone-α'-spiro-2"-5"-norbornene, the diene compound being represented by the following general formula (5):

(5)

R1, wherein in the formula (5), $R^1$ represents one selected from the group consisting of a hydrogen atom, alkyl groups having 1 to 10 carbon atoms, and a fluorine atom, the 5-norbornene-2-spiro-α-cycloalkanone-α'-spiro-2"-5"-norbornene being represented by the following general formula (1):

(1)

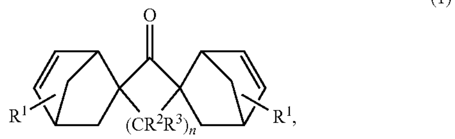

wherein $R^1$s in the formula (1) have the same meaning as that of $R^1$ in the formula (5), and $R^2$, $R^3$, and n in the formula (1) have the same meanings as those of $R^2$, $R^3$, and n in the formula (2).

3. The method for producing a 5-norbornene-2-spiro-α-cycloalkanone-α'-spiro-2"-5"-norbornene according to claim 2, wherein the acidic solvent comprises 0.01 to 2.0 mol/L of the acid.

4. The method for producing a 5-norbornene-2-spiro-α-cycloalkanone-α'-spiro-2"-5"-norbornene according to claim 2, wherein the base is at least one selected from the group consisting of amines, alkali metal hydroxides, and alkaline earth metal hydroxides.

5. The method for producing a 5-norbornene-2-spiro-α-cycloalkanone-α'-spiro-2"-5"-norbornene according to claim 2, wherein the amount of the base added to the reaction liquid is 1.0 to 10.0 equivalents to the acid.

6. The method for producing a 5-norbornene-2-spiro-α-cycloalkanone-α'-spiro-2"-5"-norbornene according to claim 2, wherein a heating temperature in the second step is 30 to 180° C.

7. The method for producing a 5-norbornene-2-spiro-α-cycloalkanone-α'-spiro-2"-5"-norbornene according to claim 2, wherein the organic solvent added to the reaction liquid is an organic solvent immiscible with a saturated hydrocarbon having 5 to 30 carbon atoms, and after a reaction, the 5-norbornene-2-spiro-α-cycloalkanone-α'-spiro-2"-5"-norbornene is liquid-liquid extracted directly from the reaction liquid with the saturated hydrocarbon having 5 to 30 carbon atoms.

8. The method for producing a 5-norbornene-2-spiro-α-cycloalkanone-α'-spiro-2"-5"-norbornene according to claim 2, comprising a step in which, after the 5-norbornene-2-spiro-α-cycloalkanone-α'-spiro-2"-5"-norbornene is formed in the second step by using an organic solvent miscible with a saturated hydrocarbon having 5 to 30 carbon atoms, the organic solvent miscible with the saturated hydrocarbon having 5 to 30 carbon atoms is removed, and then while an obtained mixture is used as it is or with water added to the obtained mixture, the 5-norbornene-2-spiro-α-cycloalkanone-α'-spiro-2"-5"-norbornene is separated by extraction with the saturated hydrocarbon having 5 to 30 carbon atoms.

9. The method for producing a 5-norbornene-2-spiro-α-cycloalkanone-α'-spiro-2"-5"-norbornene according to claim 7, further comprising after the step of separation by extraction, a step of washing, with an aqueous alkali solution and an aqueous acid solution, an extraction liquid which is obtained by separating the 5-norbornene-2-spiro-α-cycloalkanone-α'-spiro-2"-5"-norbornene by extraction using the saturated hydrocarbon having 5 to 30 carbon atoms, and which comprises the 5-norbornene-2-spiro-α-cycloalkanone-α'-spiro-2"-5"-norbornene and the saturated hydrocarbon.

10. The method for producing a 5-norbornene-2-spiro-α-cycloalkanone-α'-spiro-2"-5"-norbornene according to claim 8, further comprising after the step of separation by extraction, a step of washing, with an aqueous alkali solution and an aqueous acid solution, an extraction liquid which is obtained by separating the 5-norbornene-2-spiro-α-cycloalkanone-α'-spiro-2"-5"-norbornene by extraction using the saturated hydrocarbon having 5 to 30 carbon atoms, and which comprises the 5-norbornene-2-spiro-α-cycloalkanone-α'-spiro-2"-5"-norbornene and the saturated hydrocarbon.

* * * * *